(12) United States Patent
Amano

(10) Patent No.: US 10,980,408 B2
(45) Date of Patent: Apr. 20, 2021

(54) MEDICAL CAMERA HEAD AND MEDICAL CAMERA APPARATUS

(71) Applicant: SONY OLYMPUS MEDICAL SOLUTIONS INC., Tokyo (JP)

(72) Inventor: Kohtaro Amano, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 234 days.

(21) Appl. No.: 15/092,723

(22) Filed: Apr. 7, 2016

(65) Prior Publication Data

US 2016/0338579 A1 Nov. 24, 2016

(30) Foreign Application Priority Data

May 22, 2015 (JP) .............. JP2015-104595

(51) Int. Cl.
*A61B 1/05* (2006.01)
*H04N 5/225* (2006.01)
*A61B 1/005* (2006.01)
*A61B 1/00* (2006.01)
(Continued)

(52) U.S. Cl.
CPC .............. *A61B 1/051* (2013.01); *A61B 1/005* (2013.01); *A61B 1/00045* (2013.01); *A61B 1/053* (2013.01); *H04N 5/2251* (2013.01); *H04N 5/2253* (2013.01); *A61B 1/00006* (2013.01); *A61B 1/00009* (2013.01);
(Continued)

(58) Field of Classification Search
CPC .............. H04N 5/2251; H04N 5/2253; H04N 2005/2255; A61B 1/051; A61B 1/00045; A61B 1/005; A61B 1/053; A61B 1/00009; A61B 1/00114; A61B 1/00006; A61B 1/07; A61B 1/045
See application file for complete search history.

(56) References Cited

U.S. PATENT DOCUMENTS

2002/0080233 A1\* 6/2002 Irion .................... H04N 5/2251
348/65
2011/0064369 A1\* 3/2011 Furuyama ............ H05K 1/0274
385/129
(Continued)

FOREIGN PATENT DOCUMENTS

JP 1-161979 A 6/1989
JP 5-261065 10/1993
(Continued)

OTHER PUBLICATIONS

Office Action dated Feb. 12, 2019 in Japanese Patent Application No. 2015-104595, 5 pages.
(Continued)

*Primary Examiner* — Anner N Holder
*Assistant Examiner* — Jill D Sechser
(74) *Attorney, Agent, or Firm* — Xsensus LLP

(57) ABSTRACT

There is provided a medical camera head including an imaging board integrally including an imaging element mounting section where an imaging element is mounted, a plurality of first flexible portions whose one ends connected to the imaging element mounting section are led out of the imaging element mounting section in different directions, and a connection section connected to the other end sides of the plurality of first flexible portions.

11 Claims, 9 Drawing Sheets

(51) Int. Cl.
*A61B 1/045* (2006.01)
*A61B 1/07* (2006.01)

(52) U.S. Cl.
CPC ........... *A61B 1/00114* (2013.01); *A61B 1/045* (2013.01); *A61B 1/07* (2013.01); *H04N 2005/2255* (2013.01)

(56) References Cited

U.S. PATENT DOCUMENTS

| | | | | |
|---|---|---|---|---|
| 2011/0118549 | A1* | 5/2011 | Han | A61B 1/04 600/109 |
| 2011/0295064 | A1* | 12/2011 | Kagawa | A61B 1/04 600/110 |
| 2012/0265012 | A1* | 10/2012 | Segawa | A61B 1/00009 600/110 |
| 2014/0362286 | A1* | 12/2014 | Komi | G06K 7/10732 348/374 |
| 2018/0070805 | A1* | 3/2018 | Kawayoke | H04N 5/2253 |

FOREIGN PATENT DOCUMENTS

| | | |
|---|---|---|
| JP | 11-295617 | 10/1999 |
| JP | 2000-83896 | 3/2000 |
| JP | 2004-334 A | 1/2004 |
| JP | 2004-261362 | 9/2004 |
| JP | 2008-125590 | 6/2008 |
| JP | 2009-182869 A | 8/2009 |
| JP | 2010-177822 | 8/2010 |
| JP | 2012-85175 | 4/2012 |
| JP | 2012-195931 | 10/2012 |
| JP | 2013-056003 A | 3/2013 |

OTHER PUBLICATIONS

Japanese Office Action dated Sep. 3, 2019, issued in corresponding Japanese Patent Application No. 2015-104595.
Office Action dated May 26, 2020, issued in Japanese Patent Application No. 2015-104595, 3 pages.

* cited by examiner

MEDICAL CAMERA HEAD AND MEDICAL CAMERA APPARATUS

CROSS REFERENCE TO RELATED APPLICATIONS

This application claims the benefit of Japanese Priority Patent Application JP 2015-104595 filed May 22, 2015, the entire contents of which are incorporated herein by reference.

BACKGROUND

The present disclosure relates to medical camera heads and medical camera apparatuses.

In the medical field, camera apparatuses such as endoscope apparatuses have been used to observe an observation target in related art. Used in such a camera apparatus is a medical camera head (hereinafter also simply called a camera head) that images an observation target by an internal imaging element, such as an endoscope camera head connected to a rigid endoscope. The camera head outputs an image signal obtained by the imaging to other equipment. Then, an image of the observation target obtained by the camera apparatus is recorded, or displayed on a display apparatus to be observed by a plurality of persons during surgery. The camera head is used with a user grasping it for the purpose of moving the camera head in order to move its position in the observation target, or pressing a switch provided on the camera head in order to perform various operations of the camera head. To improve the operability of such a camera head, for example, there have been proposed technologies for reducing a camera head in size.

For example, JP 2012-195931A discloses a technology of placing a flexible board connected to an image sensor on a surface that is not provided with an imaging element, out of inner surfaces of a casing, in order to effectively use the space inside the casing.

In addition, for example, JP 2004-261362A discloses a technology of providing an external cover that is integrally molded using an elastomer material in order to reduce the number of components.

SUMMARY

Unfortunately, the existing technologies related to medical camera heads find it difficult to reduce the medical camera head in size in some cases. For example, acquiring high-definition images of the observation target increases the amount of image signals to be processed by the medical camera head. Such a case can cause, in the technologies disclosed in JP 2012-195931A and JP 2004-261362A, the need for increasing the number and width of wiring patterns that are provided for the flexible board used for transmitting the image signals and increasing the width of the flexible board itself. Therefore, the medical camera head is increased in dimension in some cases.

Hence, an embodiment of the present disclosure proposes a novel and improved medical camera head and medical camera apparatus that can be reduced in size.

According to an embodiment of the present disclosure, there is provided a medical camera head including an imaging board integrally including an imaging element mounting section where an imaging element is mounted, a plurality of first flexible portions whose one ends connected to the imaging element mounting section are led out of the imaging element mounting section in different directions, and a connection section connected to the other end sides of the plurality of first flexible portions.

According to an embodiment of the present disclosure, there is provided a medical camera apparatus including: the medical camera head; and a control apparatus configured to process an image signal from the medical camera head.

According to an embodiment of the present disclosure, a medical camera head can be reduced in size.

Note that the effects described above are not necessarily limited, and along with or instead of the effects, any effect that is desired to be introduced in the present specification or other effects that can be expected from the present specification may be exhibited.

DETAILED DESCRIPTION OF THE EMBODIMENT(S)

Figure 1:
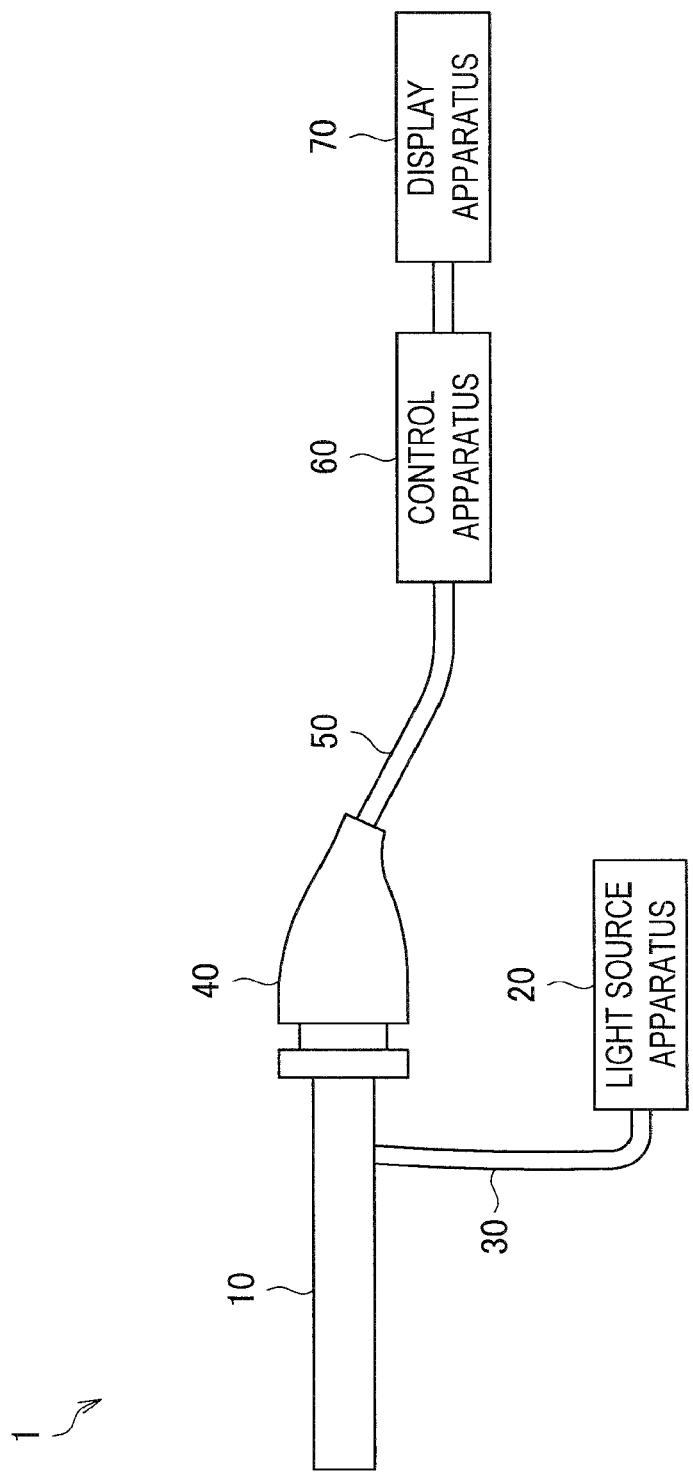
FIG. 1 is an explanatory diagram illustrating a schematic configuration of an example of an endoscope apparatus according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Description is given in the following order.
1. Endoscope apparatus according to embodiment of the present disclosure
2. Camera head according to embodiment of the present disclosure
  2-1. Schematic configuration of camera head
  2-2. Configuration of main board
  2-3. Assembly procedure
3. Effects
4. Conclusion

1. Endoscope Apparatus According to Embodiment of the Present Disclosure

First, a schematic configuration of an endoscope apparatus 1 according to an embodiment of the present disclosure will be described referring to FIG. 1.

FIG. 1 is an explanatory diagram illustrating a schematic configuration of an example of the endoscope apparatus 1 according to an embodiment of the present disclosure. The endoscope apparatus 1 is an example of a medical camera apparatus according to an embodiment of the present disclosure. The endoscope apparatus 1 includes, as illustrated in FIG. 1, an insertion section 10, a light source apparatus 20, a light guide 30, a camera head 40, a cable 50, a control apparatus 60, and a display apparatus 70.

The insertion section 10 is slender and includes therein an optical system that concentrates incident light. The front end of the insertion section 10 is inserted into a patient's body cavity, for example. The rear end of the insertion section 10 is detachably connected to the front end of the camera head 40. In addition, the insertion section 10 is connected to the light source apparatus 20 via the light guide 30, and receives light supplied from the light source apparatus 20.

The light source apparatus 20 is connected to the insertion section 10 via the light guide 30. The light source apparatus 20 supplies light to the insertion section 10 via the light guide 30. The light supplied to the insertion section 10 is emitted from the front end of the insertion section 10 to illuminate an observation target, such as a tissue inside a patient's body cavity. Reflected light from the observation target is concentrated by the optical system inside the insertion section 10.

The camera head 40 has a function of imaging the observation target. The camera head 40 is connected to the control apparatus 60 via the cable 50, which is a signal transmission section. The camera head 40 images the observation target by photoelectrically converting the reflected light from the observation target concentrated by the insertion section 10, and outputs an image signal obtained by the imaging to the control apparatus 60 via the cable 50. Note that details of the camera head 40 will be described later.

The control apparatus 60 controls the camera head 40, and also performs predetermined processing on the image signal output from the camera head 40 and then outputs the image signal to the display apparatus 70. Note that the control apparatus 60 may store an image of the observation target based on the image signal.

The display apparatus 70 displays an image of the observation target on the basis of the image signal output from the control apparatus 60. This function is implemented by, for example, a cathode ray tube (CRT) display apparatus, a liquid crystal display (LCD) apparatus, or an organic EL display (organic light emitting diode) apparatus. The image of the observation target displayed by the display apparatus 70 is observed by a plurality of persons during surgery, for example.

2. Camera Head According to Embodiment of the Present Disclosure (2-1. Schematic Configuration of Camera Head)

Next, a schematic configuration of the camera head 40 according to an embodiment of the present disclosure will be described referring to FIG. 2.

Figure 2:
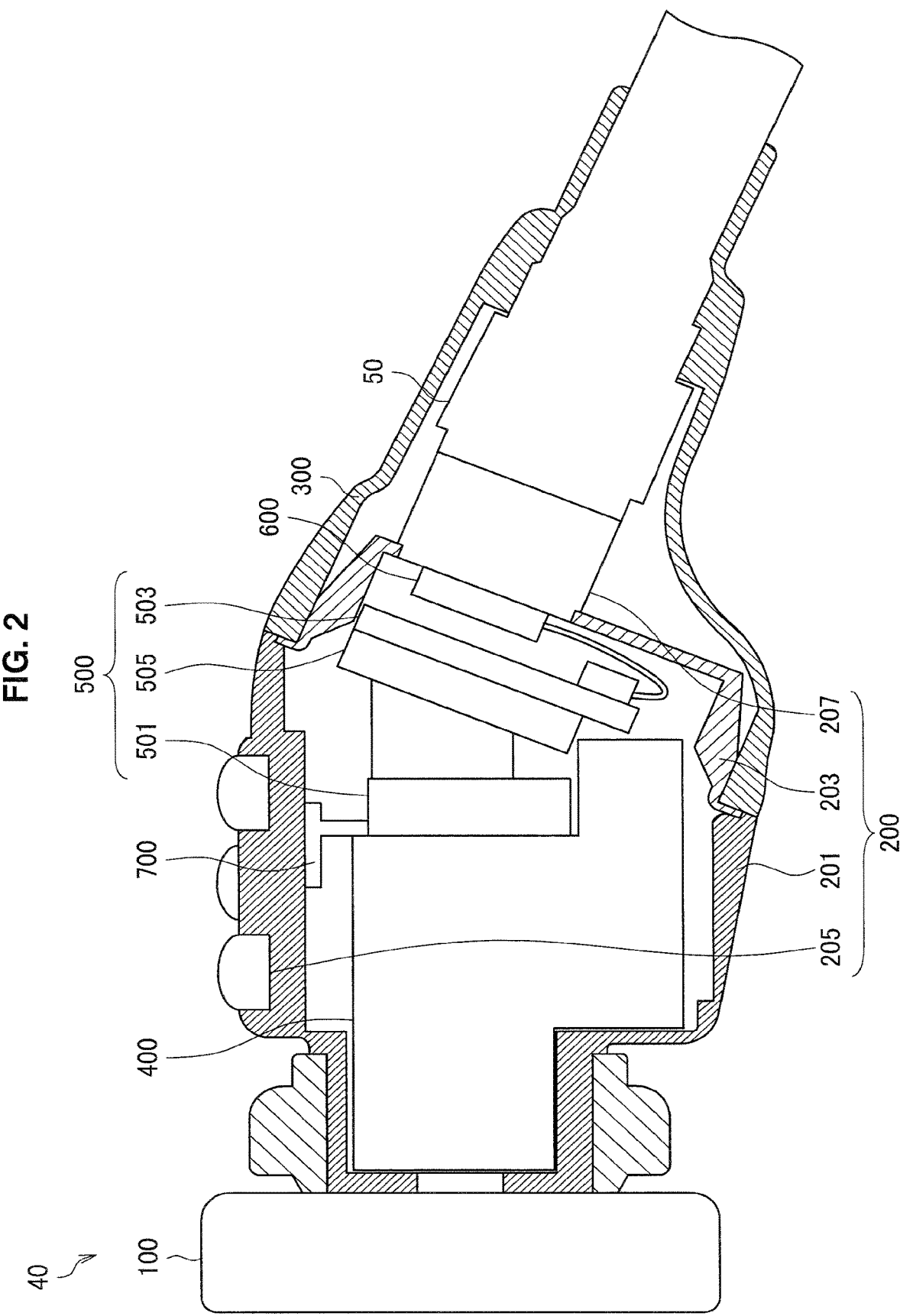
FIG. 2 is a cross-sectional view of a schematic configuration of an example of a camera head according to an embodiment of the present disclosure.

FIG. 2 is a cross-sectional view of a schematic configuration of an example of the camera head 40 according to an embodiment of the present disclosure. As illustrated in FIG. 2, the camera head 40 includes a coupler section 100, a first casing section 200, a lens unit 400, a main board 500, which is an imaging board, a connector connection board 600, and a switch connection board 700.

The coupler section 100 is provided at the front end of the camera head 40 and detachably connected to the insertion section 10. At the rear end of the coupler section 100 is provided the first casing section 200.

The first casing section 200 includes a front casing 201, a rear casing 203, a switch 205 provided on an outer circumferential surface of the front casing 201, and a cable connector 207 provided at the rear end of the rear casing 203. The first casing section 200 air-tightly accommodates the lens unit 400, the main board 500, the connector connection board 600, and the switch connection board 700. This prevents intrusion of foreign substances, such as moisture, into the first casing section 200 from the outside.

The front casing 201 and the rear casing 203 are metal casings of titanium, a titanium alloy, or SUS, for example, each having a substantially cylindrical shape, and are connected by welding, for example. To the front casing 201 of the camera head 40 is connected, from the rear casing 203 side, a second casing section 300, which is part of the cable 50, and an outer surface of the rear casing 203 is covered by the second casing section 300. These front casing 201 and rear casing 203 cover the lens unit 400, the main board 500, the connector connection board 600, and the switch connection board 700.

The switch 205 is provided on the outer circumferential surface of the front casing 201 and connected to an imaging element mounting section 501 via the switch connection board 700. One or more switches 205 are provided, for example, and a user can perform various operations by pushing the switches 205.

The cable connector 207 penetrates the rear end of the rear casing 203 and is connected to the rear casing 203 by welding, for example. The front end of the cable connector 207 is placed inside the first casing section 200, and the rear end of the cable connector 207 is placed outside the first casing section 200. The rear end of the cable connector 207 is connected to the cable 50 outside the first casing section 200.

The second casing section 300, which is part of the cable 50, is connected to the first casing section 200 of the camera head 40 and covers a connection section between the camera head 40 and the cable 50. Specifically, the second casing section 300 is placed behind the front casing 201 and connected to a rear end surface of the front casing 201. This allows the second casing section 300 to cover part of the rear casing 203, the cable connector 207, and part of the cable 50. That is, the front casing 201 of the first casing section 200 and the second casing section 300 constitute an outer surface of the camera head 40, and this portion is grasped when the user uses the camera head 40.

The lens unit 400 is provided at the front end of the first casing section 200. At the rear end of the lens unit 400 is placed the imaging element mounting section 501 where an imaging element, such as a complementary metal oxide semiconductor (CMOS) image sensor or a charge coupled device (CCD) image sensor, is mounted. The lens unit 400 concentrates the reflected light from the observation target that is emitted from the insertion section 10 connected to the coupler section 100, thereby forming an image of the observation target on an imaging surface of the imaging element. There is no particular limitation on the number of pixels and the resolution of the imaging element mounted on the imaging element mounting section 501; the number of pixels may be 1280×720, 1920×1080, 3840×2160, 7680×4320, or more, and the resolution may be high-definition television, 4K, 8K, or higher.

The main board 500 integrally includes three rigid portions: the imaging element mounting section 501 where the imaging element is mounted, a signal processing section 503 where a signal processing circuit is mounted, and an electronic component mounting section 505 where an electronic component, such as a power supply circuit, is mounted. The signal processing section 503 is electrically connected to the imaging element mounting section 501 by a flexible portion, and the signal processing section 503 is electrically connected to the electronic component mounting section 505 by a flexible portion. The main board 500 is accommodated in the first casing section 200 in a state where the flexible portions are bent. The main board 500 may be one board constituting component parts such as the imaging element mounting section 501, the signal processing section 503, the electronic component mounting section 505, and the flexible portions, or may be integrally provided by connecting at least part of the component parts that are formed separately. Note that details of an assembly procedure of the main board 500 for accommodating the main board 500 in the first casing section 200 will be described later.

The imaging element mounting section 501 photoelectrically converts, by the imaging element, the reflected light from the observation target concentrated by the lens unit 400, thereby acquiring an image signal representing the observation target. Then the imaging element mounting section 501 outputs the obtained image signal to the signal processing section 503 via the flexible portion. The signal processing section 503 performs signal processing on the image signal, a control signal, and the like output from the imaging element mounting section 501. The flexible portions connecting the signal processing section 503 and the imaging element mounting section 501 may have a plurality of wiring patterns for transmitting electrical signals output from the imaging element mounting section 501, and a signal processing circuit that converts parallel electrical signals transmitted from the at least two wiring patterns into serial signals may be mounted on the signal processing section 503. It is desirable to reduce as far as possible the size, particularly in a planar direction, of the imaging element mounting section 501, which is one factor that decides the size of the camera head 40. Hence, the imaging element mounting section 501 preferably has a shape not spreading beyond the imaging element that is mounted, and a portion spreading beyond the imaging element, if there is, is preferably as small as possible.

The signal processing section 503 is connected to the cable 50 via the connector connection board 600 and the cable connector 207. The signal processing section 503 outputs the image signal that has undergone signal processing to the cable 50 via the connector connection board 600 and the cable connector 207. The electronic component mounting section 505 mainly performs power supply to the signal processing section 503, power control, and the like. Note that details of the main board 500 will be described later.

The connector connection board 600 couples the signal processing section 503 to the cable connector 207. The connector connection board 600 includes two rigid portions and a flexible portion coupling the two rigid portions. One rigid portion is connected to the rear end of the signal processing section 503, and the other rigid portion is connected to the front end of the cable connector 207.

The switch connection board 700 couples the imaging element mounting section 501 to the switch 205. The switch connection board 700 may be, for example, a flexible board.

(2-2. Configuration of Main Board)

The preceding section has described the schematic configuration of the camera head 40 according to an embodiment of the present disclosure. Next, a configuration of the main board 500 according to an embodiment of the present disclosure will be described referring to FIG. 3.

Figure 3:
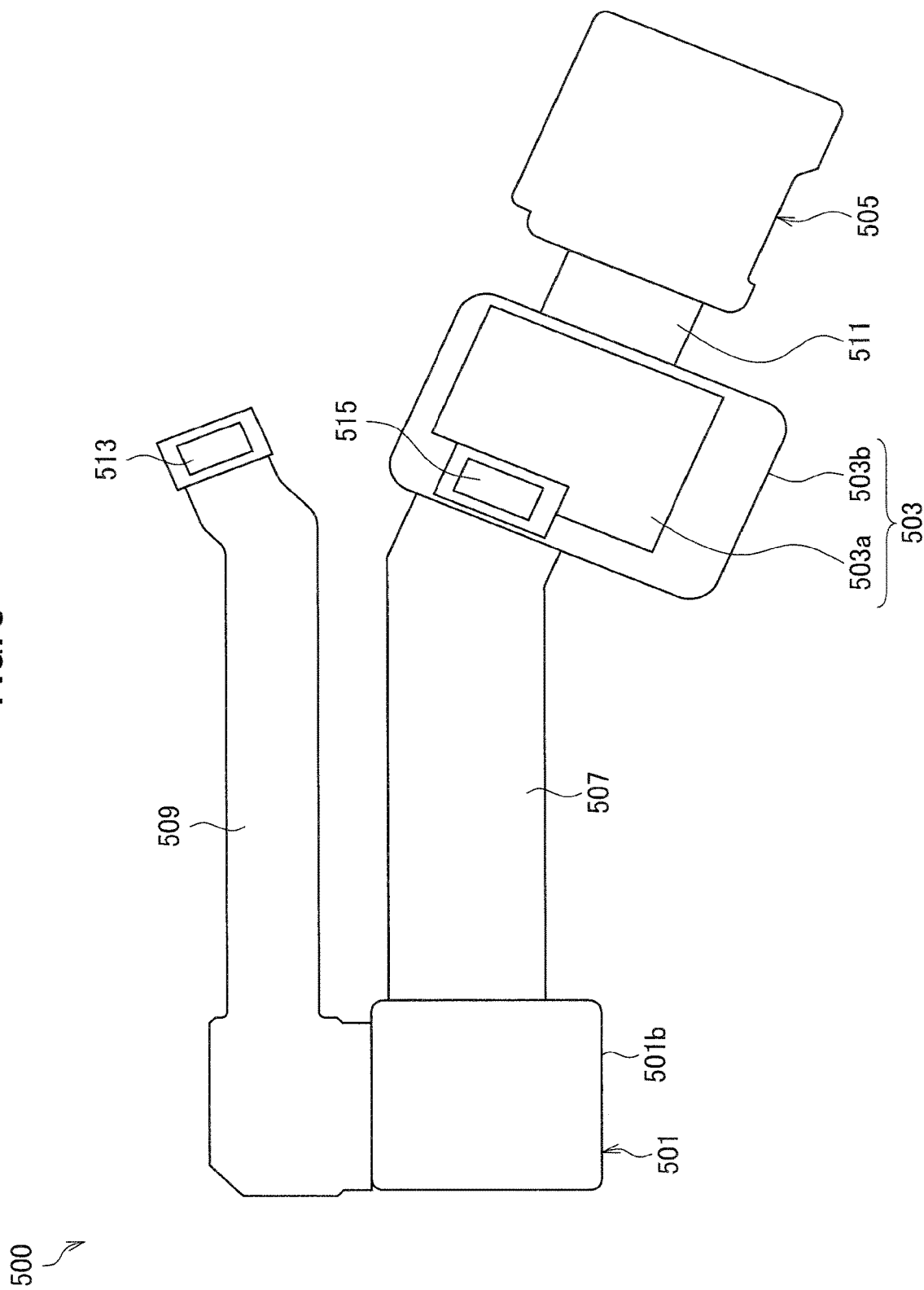
FIG. 3 is a developed view of an example of a configuration of a main board according to an embodiment of the present disclosure.

FIG. 3 is a developed view of an example of the configuration of the main board 500 according to an embodiment of the present disclosure. As illustrated in FIG. 3, the main board 500 mainly includes three rigid portions (the imaging element mounting section 501, the signal processing section 503, and the electronic component mounting section 505), flexible portions 507, 509, and 511, and a connector 513. The main board 500 is fabricated by stacking the rigid portions on an integral flexible board. The integral flexible board is obtained by, for example, blanking a long flexible wiring board material, which is a raw workpiece. Hereinafter, a surface of the main board 500 that is illustrated in FIG. 3 will be called an upper surface, and a surface of the main board 500 that is not illustrated in FIG. 3 will be called a lower surface. In FIG. 3, the imaging element is mounted on a lower surface 501b (not illustrated) of the imaging element mounting section 501.

The main board 500 includes a plurality of flexible portions whose one ends connected to the imaging element mounting section 501 are led out of the imaging element mounting section 501 in different directions. In other words, a plurality of flexible portions are connected to a plurality of sides of the imaging element mounting section 501 so that a plurality of wiring patterns can be provided distributedly at a plurality of sides of the imaging element mounting section 501 having a substantially polygonal shape, such as a substantially rectangular shape. Specifically, as illustrated in FIG. 3, in the main board 500, one end of the flexible portion 507 and one end of the flexible portion 509 are connected to edge portions of the substantially rectangular imaging element mounting section 501 that are orthogonal to each other, and are led out of the edge portions in directions orthogonal to each other. Note that the number of the flexible portions connected to the imaging element mounting section 501 illustrated in FIG. 3 is a mere example, and three or more flexible portions may be connected to the imaging element mounting section 501.

As illustrated in FIG. 3, the flexible portion 507 extends in the direction in which it is led out of the imaging element mounting section 501, and couples the imaging element mounting section 501 to the signal processing section 503. In addition, the flexible portion 509 bends in a direction perpendicular to the direction in which it is led out of the imaging element mounting section 501, and extends in the same direction as the direction in which the flexible portion 507 extends. Therefore, the extending portion of the flexible portion 509 is provided parallel to the extending portion of the flexible portion 507 with a constant spacing therebetween.

If the flexible portion 509 extends in the direction in which it is led out of the imaging element mounting section 501, the flexible portion 509 extends in a direction going away from the flexible portion 507. In this case, the raw workpiece for forming the integral flexible board constituting the main board 500 is increased in size. Hence, the integral flexible board constituting the main board 500 is made to have the shape as illustrated in FIG. 3; thus, the raw workpiece for fabricating the main board 500 can be reduced in dimension, as compared with the case where the flexible portions 507 and 509 extend in the directions in which they are led out of the imaging element mounting section 501.

At least one of the plurality of flexible portions whose one ends are connected to the imaging element mounting section 501 has, when being bent, an overlap portion that overlaps with another flexible portion connected to the imaging element mounting section 501. Specifically, the flexible portion 509 is provided so as to overlap with the flexible portion 507 when being bent at a line along a connection portion between the flexible portion 509 and the imaging element mounting section 501. Therefore, the overlapped flexible portions 507 and 509 can be bent by one step.

At least one of the plurality of flexible portions whose one ends are connected to the imaging element mounting section 501 is provided with a connector connected to the signal processing section 503 at the other end. Specifically, the other end of the flexible portion 509 is provided with the connector 513 connected to the signal processing section 503. Note that the other end of the flexible portion 507 may be provided with a connector connected to the signal processing section 503.

The signal processing section 503 is a connection section connected to the other end sides of the plurality of flexible portions whose one ends are connected to the imaging element mounting section 501. Specifically, the other end side of the flexible portion 507 is connected to an edge portion of the substantially rectangular signal processing section 503, and the other end side of the flexible portion 509 is connected, via the connector 513, to a portion close to the edge portion on an upper surface 503a of the signal processing section 503. The main board 500 is provided with a connector section where the signal processing section 503 and at least one of the plurality of flexible portions whose one ends are connected to the imaging element mounting section 501 are detachably connected to each other. Specifically, the upper surface 503a of the signal processing section 503 is provided with a connector receptacle 515 for connecting the connector 513. The connector 513 and the connector receptacle 515 constitute the connector section.

In the present embodiment, the configuration including the connector 513 and the connector receptacle 515 is described as an example of a connector section. Without being limited to this example, any configuration that allows the flexible portion 509 to be detachably connected may be employed, such as a configuration in which the other end of the flexible portion 509 is provided with an exposed portion where a wiring pattern is partly exposed, and the upper surface 503a is provided with a connector having a contact portion that holds the other end of the flexible portion 509 and is in contact with and electrically connected to the exposed portion, or a configuration in which an end portion of the signal processing section 503 is provided with an exposed portion where a wiring pattern is partly exposed, and the flexible portion 509 is provided with a connector having a contact portion that holds the end portion of the signal processing section 503 and is in contact with and electrically connected to the exposed portion. In addition, without being limited to the configuration in which the connector 513 is provided at the other end of the flexible portion 509, the connector 513 may be provided at a place other than an end portion, such as some midpoint on the extending flexible portion 509, as long as the place is on the other end side of the flexible portion 509, which is different from the one end connected to the imaging element mounting section 501. A lower surface 503b of the signal processing section 503 is connected to the connector connection board 600 illustrated in FIG. 2.

The electronic component mounting section 505 is connected to the signal processing section 503 via the flexible portion 511. The flexible portion 511, whose end portions are connected to an edge portion of the signal processing section 503 and an edge portion of the electronic component mounting section 505 that face each other when the main board 500 is developed, couples the signal processing section 503 to the electronic component mounting section 505. The length of the flexible portion 511 is set to a length that allows it to be bent substantially 180° at a line along a connection portion between the flexible portion 511 and the signal processing section 503 to make the signal processing section 503 and the electronic component mounting section 505 overlap with each other.

(2-3. Assembly Procedure)

The preceding section has described the configuration of the main board 500 according to an embodiment of the present disclosure. Next, an assembly procedure of the main board 500 according to an embodiment of the present disclosure for accommodating the main board 500 in the first casing section 200 will be described referring to FIGS. 4 to 9.

Figure 4:
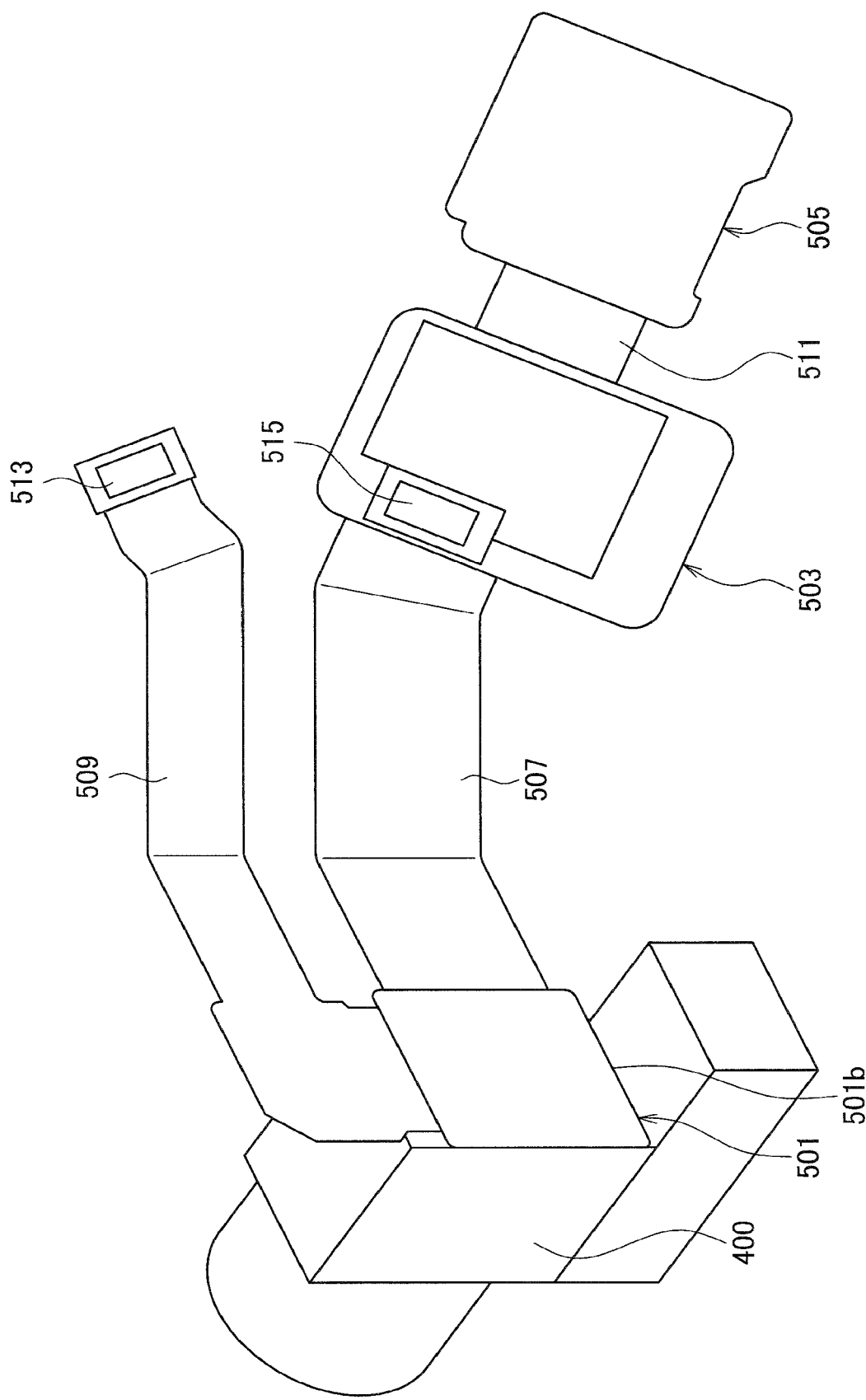
FIG. 4 is an explanatory diagram for explaining an assembly procedure of a main board according to an embodiment of the present disclosure.

In assembling the main board 500, first, a rear end surface of the lens unit 400 is connected to the imaging element mounting section 501, as illustrated in FIG. 4. In FIG. 4, the rear end surface of the lens unit 400 and the lower surface 501b of the imaging element mounting section 501 on which the imaging element is mounted are arranged to face each other. The imaging element mounting section 501 is fixed to the lens unit 400 with a screw, for example.

Figure 5:
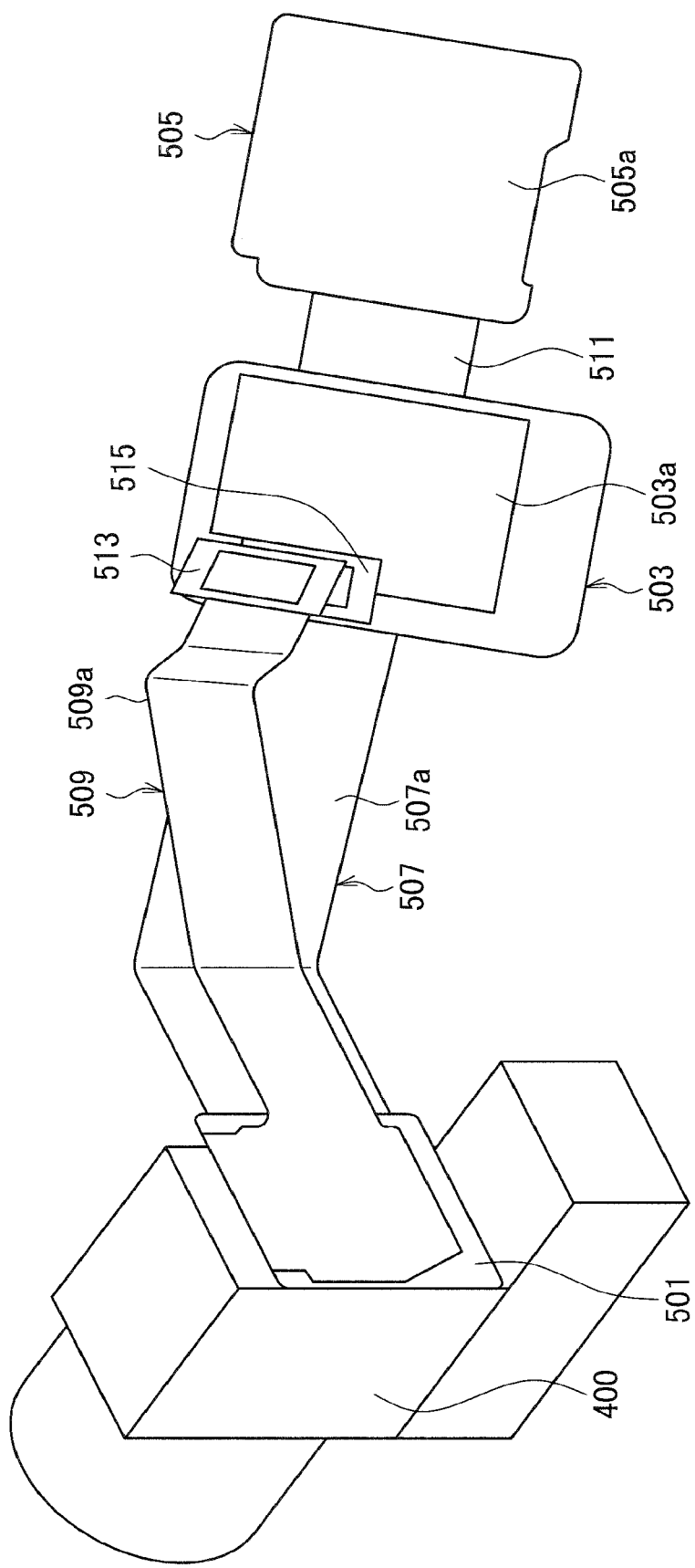
FIG. 5 is an explanatory diagram for explaining the assembly procedure of the main board according to an embodiment of the present disclosure.

Next, as illustrated in FIG. 5, the flexible portion 509 is bent so as to make an upper surface 509a of the flexible portion 509 and an upper surface 507a of the flexible portion 507 face each other. Specifically, by being bent at a line along a connection portion between the flexible portion 509 and the imaging element mounting section 501, the flexible portion 509 is provided with an overlap portion that at least partly overlaps with the flexible portion 507. Then, the connector 513 provided at the other end of the flexible portion 509 is connected to the connector receptacle 515 provided on the upper surface 503a of the signal processing section 503.

Figure 6:
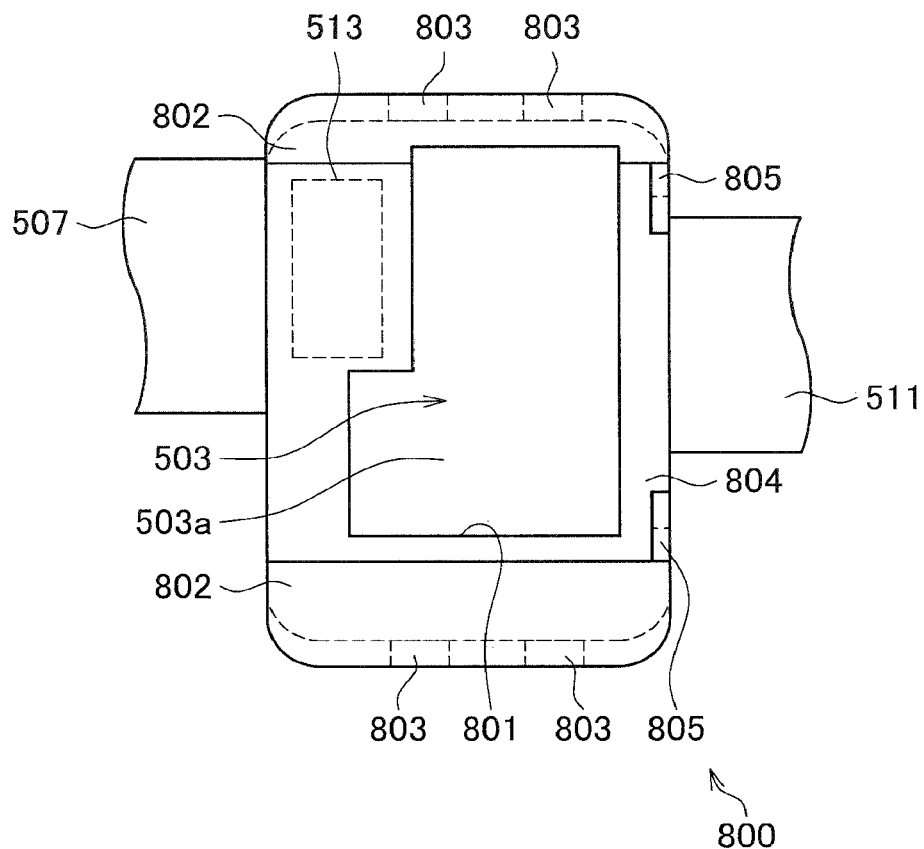
FIG. 6 is an explanatory diagram for explaining the assembly procedure of the main board according to an embodiment of the present disclosure.
Figure 7:
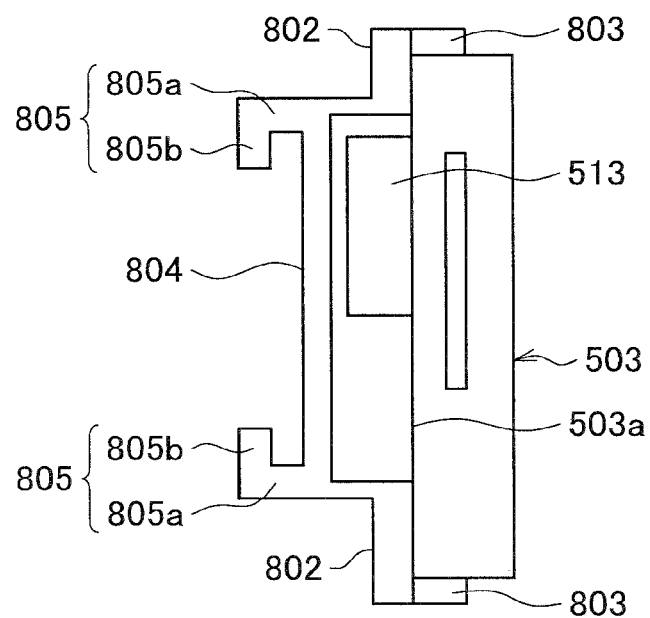
FIG. 7 is an explanatory diagram for explaining the assembly procedure of the main board according to an embodiment of the present disclosure.

Next, the upper surface 503a of the signal processing section 503 is equipped with a cover member 800. The cover member 800 is provided to restrict a relative position of the connector 513 with respect to the signal processing section 503. The cover member 800 is fixed to the upper surface 503a side of the signal processing section 503 with a screw, for example. FIG. 6 is a front view of the signal processing section 503 equipped with the cover member 800, and FIG. 7 is a right side view of the signal processing section 503 equipped with the cover member 800. As illustrated in FIGS. 6 and 7, the cover member 800 provided on the signal processing section 503 covers the connector section that is constituted by the connector 513 of the flexible portion 509 connected to the signal processing section 503 and the connector receptacle 515 of the signal processing section 503.

The cover member 800 has substantially the same external shape as the signal processing section 503, and includes a pair of cover connection portions 802 connected to the signal processing section 503 at a pair of edge portions of the signal processing section 503, and a cover portion 804 protruding from the pair of cover connection portions 802 toward the side opposite to the signal processing section 503. Between the cover portion 804 and the signal processing section 503 is formed a space, where the connector 513 is placed.

Figure 9:
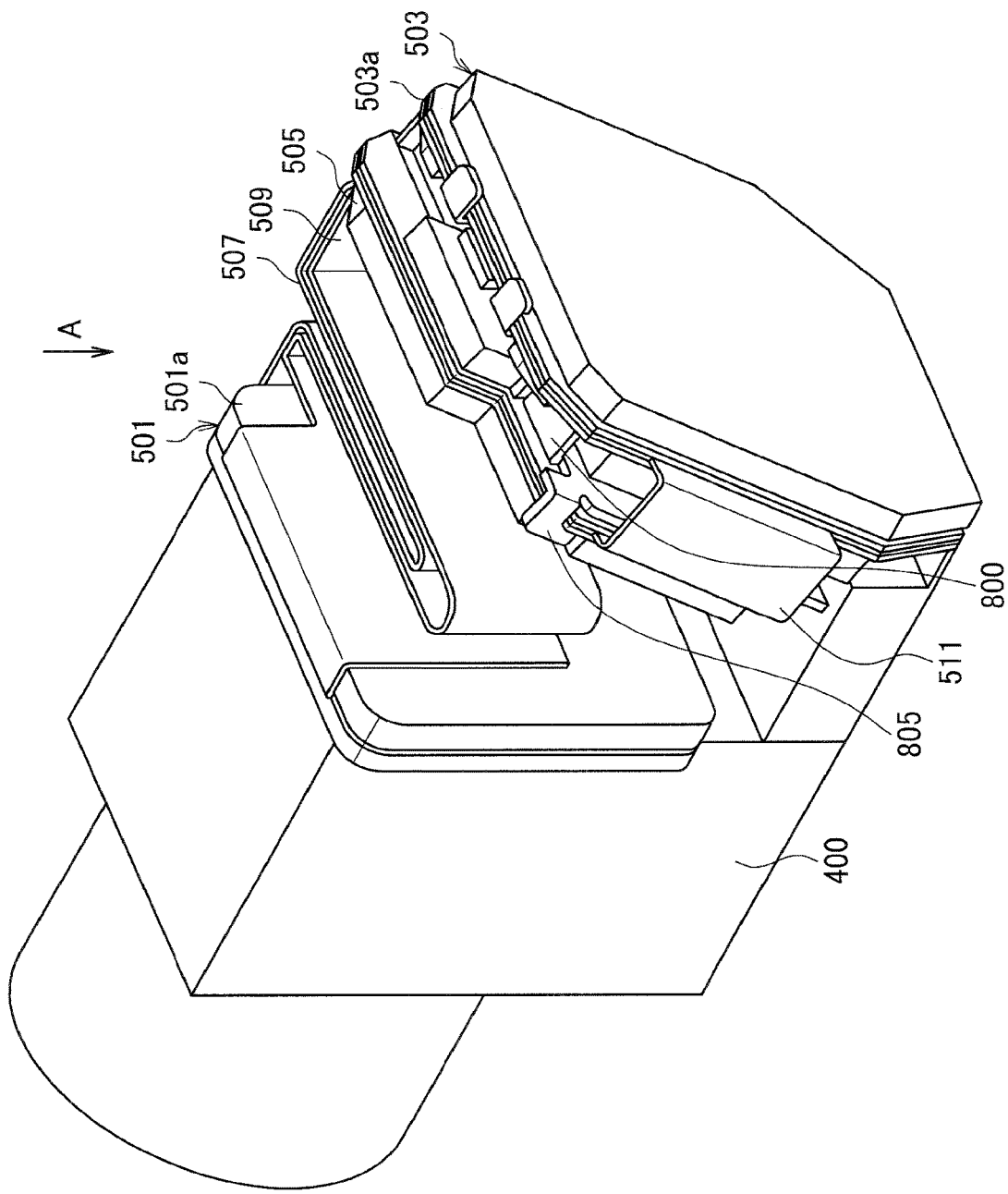
FIG. 9 is an explanatory diagram for explaining the assembly procedure of the main board according to an embodiment of the present disclosure.

An opening 801 is formed at the center of the cover portion 804. The shape of the opening 801 may be a polygonal shape, a circular shape, an elliptical shape, or a combination of any of these shapes. For example, the shape of the opening 801 can be decided in consideration of the strength and weight of the cover member 800, and further, in consideration of providing a space for bending of the flexible portions 507 and 509 and providing a space for preventing interference of the signal processing section 503 and the electronic component mounted on the electronic component mounting section 505, as illustrated in FIG. 9. The opening 801 is not provided in a position corresponding to the connector 513 connected to the signal processing section 503, as illustrated in FIG. 6. Thus, the connector 513 is covered by the cover member 800 and its relative position with respect to the signal processing section 503 is restricted.

The cover connection portions 802 are provided with first fastening portions 803. One or more first fastening portions 803 are provided at each of outer edge portions of the cover member 800 that face each other, in order to fix the cover member 800 to the signal processing section 503. The first fastening portions 803 protrude in a direction in which the cover member 800 faces the signal processing section 503, as illustrated in FIG. 7. The plurality of first fastening portions 803 are fastened to edge portions that are not connected to a flexible portion, out of the edge portions of the signal processing section 503, to sandwich the signal processing section 503.

The cover portion 804 is provided with second fastening portions 805. The second fastening portions 805 are provided to sandwich the electronic component mounting section 505, and for example, a pair of the second fastening portions 805 is provided above the edge portion of the signal processing section 503 that is connected to the flexible portion 511. As illustrated in FIG. 7, the pair of second fastening portions 805 includes protruding portions 805a protruding in a direction opposite to the direction in which the first fastening portions 803 protrude, and extending portions 805b that are provided at the tips of the protruding portions 805a and extend in directions facing each other.

Figure 8:
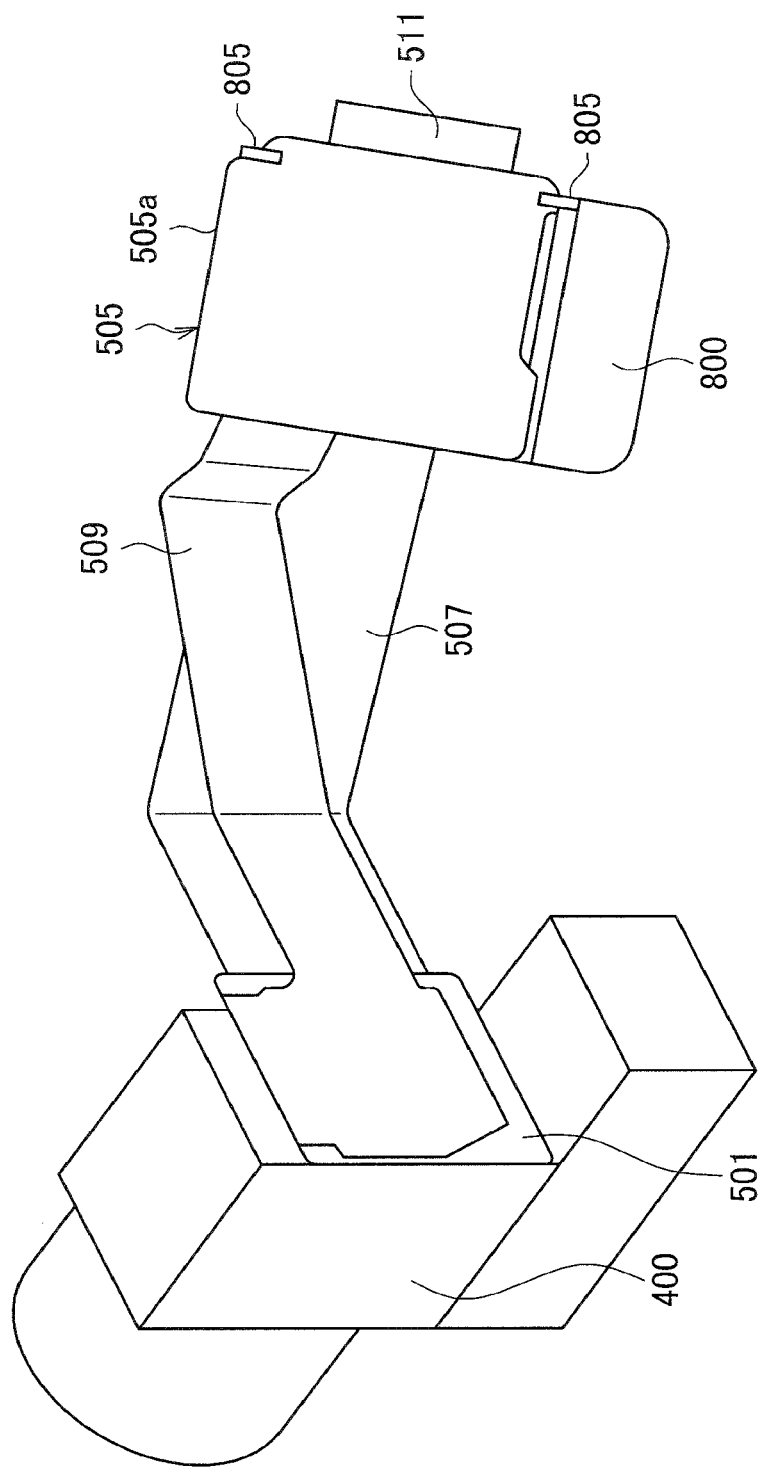
FIG. 8 is an explanatory diagram for explaining the assembly procedure of the main board according to an embodiment of the present disclosure.

Next, as illustrated in FIG. 8, the flexible portion 511 is bent and the electronic component mounting section 505 and the signal processing section 503 are arranged to face each other with the cover member 800 placed therebetween. Specifically, an upper surface 505a of the electronic component mounting section 505 and the upper surface 503a of the signal processing section 503 are arranged to face each other with the cover member 800 placed therebetween. Here, the edge portion of the electronic component mounting section 505 that is connected to the flexible portion 511 is fastened to the extending portions 805b of the second fastening portions 805. Thus, the movement of the electronic component mounting section 505 is restricted by the pair of second fastening portions 805. The electronic component mounting section 505 overlapped with the signal processing section 503 is fixed with a screw, for example, to the cover member 800 fixed to the signal processing section 503.

Next, as illustrated in FIG. 9, the flexible portions 509 and 507 are bent in a state of being overlapped with each other to be provided with the overlap portion, and the imaging element mounting section 501 and the signal processing section 503 are arranged to face each other. Specifically, an upper surface 501a of the imaging element mounting section 501 and the upper surface 503a of the signal processing section 503 are arranged to face each other. At this time, the electronic component mounting section 505 is placed between the imaging element mounting section 501 and the signal processing section 503.

Figure 10:
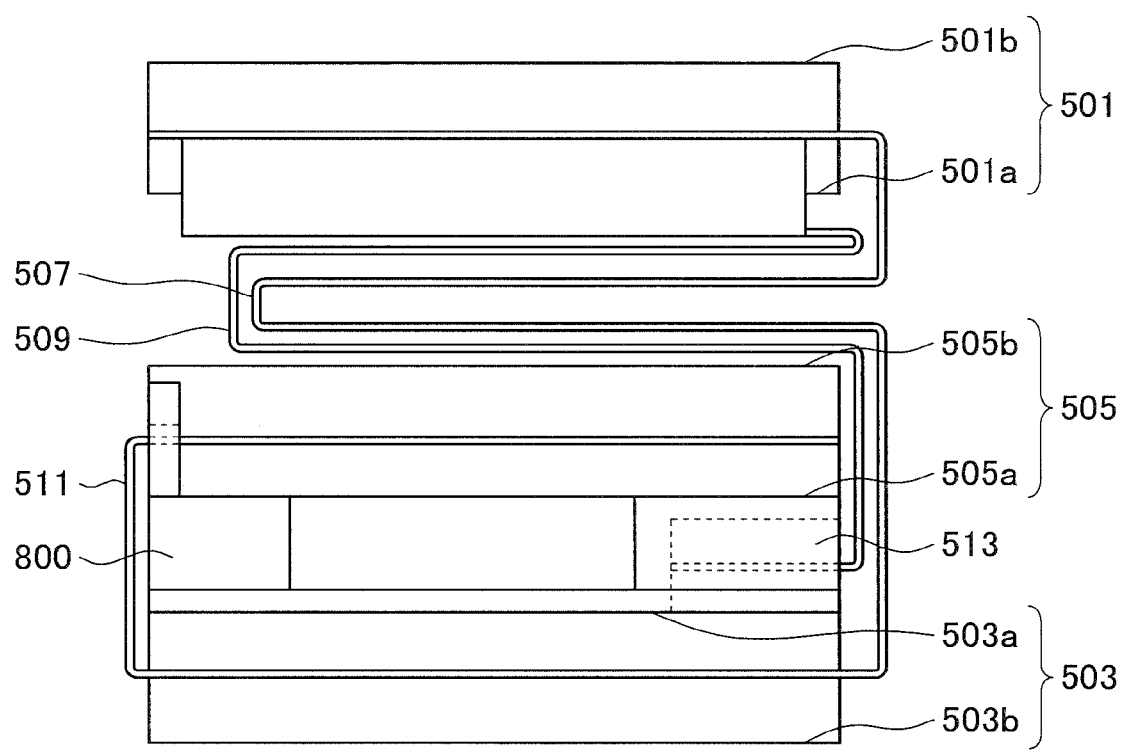
FIG. 10 is a schematic diagram illustrating a stacked state of the main board illustrated in FIG. 9.

FIG. 10 is a schematic diagram illustrating a stacked state of the main board 500 assembled as in FIG. 9, and illustrates the state viewed in the A direction shown in FIG. 9. As illustrated in FIG. 10, at least part of the overlap portion where the flexible portions 507 and 509 overlap with each other is placed between the upper surface 501a of the imaging element mounting section 501 and the upper surface 503a of the signal processing section 503. Specifically, the overlapped flexible portions 507 and 509 are bent to be placed between the upper surface 501a of the imaging element mounting section 501 and a lower surface 505b of the electronic component mounting section 505. In addition, as illustrated in FIG. 10, the upper surface 503a of the signal processing section 503 on which the connector section constituted by the connector 513 and the connector receptacle 515 is positioned faces the upper surface 501a of the imaging element mounting section 501.

Through the above procedure, the main board 500 is assembled into a substantially rectangular parallelepiped shape and accommodated in the camera head 40. Note that the imaging element mounting section 501 may be connected to the connector connection board 600 before the bending of the flexible portions 507 and 509 described using FIG. 9. The signal processing section 503 is fixed to the rear casing 203 illustrated in FIG. 2 with a screw.

The smaller the difference in length between the flexible portions 507 and 509 that are overlapped is, the smaller the force for bending the overlapped flexible portions 507 and 509 can be. This facilitates assembly work. In addition, the smaller the difference in length between the flexible portions 507 and 509 that are overlapped is, the smaller the restoring force of the flexible portions 507 and 509 after the bending of the overlapped flexible portions 507 and 509 can be. This suppresses deformation and failure of components inside the camera head 40.

3. Effects

According to the above-described embodiment, a plurality of flexible portions are connected to the imaging element mounting section 501 where the imaging element is mounted. One ends of the plurality of flexible portions connected to the imaging element mounting section 501 are led out of the imaging element mounting section 501 in different directions, and the other end sides of the plurality of flexible portions are connected to the signal processing section 503. Therefore, even when the amount of image signals to be processed by the camera head is increased, it is possible to suppress an increase in dimension of the imaging element mounting section that is connected to the flexible portion used for transmitting the image signals.

In other words, a plurality of flexible portions are connected to a plurality of sides of the imaging element mounting section so that a plurality of wiring patterns can be provided distributedly at a plurality of sides of the imaging element mounting section having a substantially polygonal shape, such as a substantially rectangular shape. Thus, even when the amount of image signals to be processed by the camera head is increased and the number and width of wiring patterns that are provided for the flexible board used for transmitting the image signals are increased, it is possible to suppress an increase in dimension of the imaging element mounting section in the planar direction caused by aggregating a plurality of wiring patterns at one side of the imaging element mounting section having a substantially polygonal shape. Consequently, the camera head can be reduced in size.

In addition, according to an embodiment, the imaging element mounting section 501 and the signal processing section 503 are arranged to face each other. Therefore, placing another member in a layer structure between the imaging element mounting section 501 and the signal processing section 503 allows the other member to be accommodated in a columnar space whose bottom surface is the imaging element mounting section 501. Thus, suppression of an increase in dimension of the imaging element mounting section is accompanied by suppression of an increase in dimension of the casing of the camera head in the planar direction of the imaging element mounting section.

In addition, according to an embodiment, at least one of the plurality of flexible portions whose one ends are connected to the imaging element mounting section 501 has, when being bent, an overlap portion that overlaps with at least one of the other flexible portions connected to the imaging element mounting section 501. At least part of the overlap portion is placed between the imaging element mounting section 501 and the signal processing section 503. Therefore, the plurality of flexible portions can be placed in a layer structure between the imaging element mounting section and the signal processing section. Consequently, a space occupied by the flexible portions provided inside the casing of the camera head can be reduced.

In addition, according to an embodiment, the main board 500 is provided with a connector section where the signal processing section 503 and at least one of the plurality of flexible portions whose one ends are connected to the imaging element mounting section 501 are detachably connected to each other. Therefore, the flexible portions can be connected to the signal processing section by a simple method. This facilitates the assembly of the camera head.

In addition, according to an embodiment, the connector section constituted by the connector 513 and the connector receptacle 515 is positioned on a surface of the signal processing section 503 that faces the imaging element mounting section 501, and the signal processing section 503 is provided with the cover member 800 that covers the connector section. Therefore, the cover member can restrict a relative position of the connector 513 with respect to the connector receptacle 515 of the signal processing section 503. Consequently, poor connection of the connector section, such as poor fit (e.g., oblique connection of the connector to the connector receptacle) and disconnection of the connector from the connector receptacle, can be suppressed.

In addition, according to an embodiment, the electronic component mounting section 505 connected to the signal processing section 503 via the flexible portion is further provided. Therefore, as compared with the case where the signal processing section 503 and the electronic component mounting section 505 are integrally formed, each rigid portion can be reduced in dimension. Consequently, placing the signal processing section and the electronic component mounting section in a layer structure reduces a space occupied by the rigid portion for performing signal processing on the image signals provided inside the casing of the camera head.

In addition, according to an embodiment, the flexible portion connecting the signal processing section 503 and the electronic component mounting section 505 is bent, and the electronic component mounting section 505 is placed between the imaging element mounting section 501 and the signal processing section 503. Therefore, as compared with the case where the signal processing section is placed between the imaging element mounting section and the electronic component mounting section, the distance between the signal processing section and another member, such as the cable connector, can be reduced. Consequently, a member that couples the signal processing section to the other member can be reduced in size.

In addition, according to an embodiment, the flexible portions connecting the signal processing section 503 and the imaging element mounting section 501 have a plurality of wiring patterns for transmitting electrical signals output from the imaging element mounting section 501, and a signal processing circuit that converts parallel electrical signals transmitted from the at least two wiring patterns into serial signals is mounted on the signal processing section 503. Therefore, the amount of signals lines output from the signal processing section 503 can be reduced. Consequently, it is possible to reduce the number of wiring patterns for output from the signal processing section on the main board 500, the number of signal lines used for transmitting signals to be output to the outside of the camera head, and further, the size of a connection section on the main board 500 for connecting the signal lines.

4. Conclusion

As described above, according to an embodiment of the present disclosure, the imaging element is mounted on the imaging element mounting section, and one ends of the plurality of flexible portions connected to the imaging element mounting section are led out of the imaging element mounting section in different directions, and the other end sides of the plurality of flexible portions are connected to the connection section. Therefore, even when the amount of image signals to be processed by the camera head is increased, it is possible to suppress an increase in dimension of the imaging element mounting section that is connected to the flexible portion used for transmitting the image signals. Consequently, the camera head can be reduced in size.

Described above is an example in which the camera head according to an embodiment of the present disclosure is used for an endoscope apparatus, but a medical camera apparatus including the camera head according to an embodiment of the present disclosure is not limited to this example. For example, the medical camera apparatus according to an embodiment of the present disclosure may be a medical microscope apparatus. The medical microscope apparatus is a camera apparatus used for carrying out surgical operations while observing a portion to be operated on under magnification. The medical microscope apparatus includes an imaging apparatus and an arm apparatus capable of holding the imaging apparatus and moving and fixing a position and an attitude of the imaging apparatus. The camera head according to an embodiment of the present disclosure can be, for example, used as the imaging apparatus of such a medical microscope apparatus. In addition, the signal transmission section according to an embodiment of the present disclosure can be, for example, used as the arm apparatus of such a medical microscope apparatus. In such a medical microscope apparatus, the arm apparatus may hold two camera heads.

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1) A medical camera head including an imaging board integrally including
an imaging element mounting section where an imaging element is mounted,
a plurality of first flexible portions whose one ends connected to the imaging element mounting section are led out of the imaging element mounting section in different directions, and
a connection section connected to the other end sides of the plurality of first flexible portions.

(2) The medical camera head according to (1),
wherein the imaging element mounting section and the connection section of the imaging board are arranged to face each other.

(3) The medical camera head according to (1) or (2),
wherein, when being bent, at least one of the plurality of first flexible portions of the imaging board has an overlap portion that overlaps with at least one of the other first flexible portions, and at least part of the overlap portion is placed between the imaging element mounting section and the connection section.

(4) The medical camera head according to any one of (1) to (3),
wherein the imaging board is provided with a connector section where the connection section and at least one of the first flexible portions are detachably connected to each other.

(5) The medical camera head according to (4),
wherein the connector section is positioned on a surface of the connection section that faces the imaging element mounting section, and the connection section is provided with a cover member configured to cover the connector section.

(6) The medical camera head according to any one of (1) to (5),
wherein the imaging board further includes an electronic component mounting section connected to the connection section via a second flexible portion.

(7) The medical camera head according to (6),
wherein the second flexible portion of the imaging board is bent, and
wherein the electronic component mounting section is placed between the imaging element mounting section and the connection section.

(8) The medical camera head according to any one of (1) to (7),
wherein the plurality of first flexible portions of the imaging board have a plurality of wiring patterns for transmitting electrical signals output from the imaging element mounting section, and
wherein a signal processing circuit configured to convert parallel electrical signals transmitted from the at least two wiring patterns into serial signals is mounted on the connection section.

(9) A medical camera apparatus including:
the medical camera head according to any one of (1) to (8); and
a control apparatus configured to process an image signal from the medical camera head.

(10) A medical camera head including an imaging board integrally including
an imaging element mounting section where an imaging element is mounted, the imaging element mounting section having a substantially polygonal planar shape,
a plurality of first flexible portions whose one ends are connected to a respective plurality of sides of the imaging element mounting section, and
a connection section connected to the other end sides of the plurality of first flexible portions.

What is claimed is:

1. A medical camera head comprising:
an imaging board integrally including an imaging element mount where an imaging circuit is mounted;
a signal processing board arranged to face the imaging element mount and configured to process input image signals;
a plurality of first flexible wires extending along an entire length of a first flexible portion connecting the signal processing board to the imaging board, each of the plurality of first flexible wires having one end connected to a connection section at different location on the imaging element mount than where the imaging circuit is mounted and another end connected to the signal processing board and configured to transmit the image signals from the imaging element mount to the signal processing board; and
a plurality of second flexible wires in a second flexible portion, different from the first flexible portion, connecting the signal processing board to the imaging board,
wherein, when bent, the plurality of first flexible wires has an overlap portion that overlaps with the second flexible wires, and at least part of the overlap portion is placed between the imaging element mount and the signal processing board,
wherein the plurality of first flexible wires are led out of the imaging element mount in a direction which is orthogonal to a direction that the plurality of second flexible wires are led out from the imaging element mount.

2. The medical camera head according to claim 1,
wherein the imaging board includes a connector section where the connection section and the first flexible portion are detachably connected to each other.

3. The medical camera head according to claim 2,
wherein the connector section is positioned on a surface of the connection section that faces the imaging element mounting section, and the connection section includes a cover to cover the connector section.

4. The medical camera head according to claim 1, further comprising:
an electronic component mounting section connected to the signal processing board via third flexible wires of a third flexible portion.

5. The medical camera head according to claim 4,
wherein the third flexible portion is bent, and
wherein the electronic component mounting section is disposed between the imaging element mounting section and the connection section.

6. The medical camera head according to claim 1,
wherein the plurality of first flexible wires of the imaging board have a plurality of wiring patterns for transmitting electrical signals output from the imaging element mounting section, and wherein a signal processing circuit configured to convert parallel electrical signals transmitted from the at least two wiring patterns into serial signals is mounted on the connection section.

7. The medical camera head according to claim 1, further comprising:
a connector to connect the first flexible portion to the signal processing board.

8. The medical camera head according to claim 1, further comprising:
a connector to connect the second flexible portion to the imaging board.

9. The medical camera head according to claim 1, further comprising:
a connector to connect the first flexible portion to the signal processing board, and
a connector to connect the second flexible portion to the imaging board.

10. A medical camera apparatus comprising:
the medical camera head according to claim 1; and
a control apparatus configured to process an image signal from the medical camera head.

11. A medical camera head comprising:
an imaging board integrally including an imaging element mount where an imaging circuit is mounted;
a signal processing board arranged to face the imaging element mount and configured to process input image signals;
a plurality of first flexible wires in a first flexible portion connecting the signal processing board to the imaging board, each of the plurality of first flexible wires having one end connected to a connection section at different location on the imaging element mount than where the imaging circuit is mounted and another end connected to the signal processing board and configured to transmit the image signals from the imaging element mount to the signal processing board; and
a plurality of second flexible wires in a second flexible portion, different from the first flexible portion, connecting the signal processing board to the imaging board,
wherein, when bent, the plurality of first flexible wires has an overlap portion that overlaps with the second flexible wires, and at least part of the overlap portion is placed between the imaging element mount and the signal processing board,
wherein the plurality of first flexible wires are led out of the imaging element mount in a direction which is orthogonal to a direction that the plurality of second flexible wires are led out from the imaging element mount.

* * * * *